United States Patent [19]

Beran

[11] Patent Number: 5,066,140

[45] Date of Patent: Nov. 19, 1991

[54] TEMPERATURE MEASUREMENT

[75] Inventor: Anthony V. Beran, Santa Ana, Calif.

[73] Assignee: Respiratory Support Products, Inc., Irvine, Calif.

[21] Appl. No.: 107,989

[22] Filed: Oct. 13, 1987

[51] Int. Cl.[5] .......................... G01K 7/02; G01K 7/22; H03H 11/00

[52] U.S. Cl. .................................. 374/134; 307/117; 324/710; 333/213; 374/179

[58] Field of Search .............. 374/181, 182, 184, 178, 374/134; 333/213, 216; 307/117

[56] References Cited

U.S. PATENT DOCUMENTS

| | | | |
|---|---|---|---|
| 3,069,909 | 12/1962 | Hines | 374/192 X |
| 3,434,349 | 3/1969 | Frischmann | 374/182 |
| 3,580,074 | 5/1971 | Wescott | 73/304 C |
| 3,582,761 | 6/1971 | Ball, Jr. | 322/2 |
| 3,688,580 | 9/1972 | Jarzembski | 374/182 |
| 3,725,783 | 4/1973 | Alton et al. | 324/710 |
| 3,906,391 | 9/1975 | Murdock . | |
| 4,157,663 | 6/1979 | Ihlenfeldt et al. | 374/182 X |
| 4,161,880 | 7/1979 | Prosky | 374/194 X |
| 4,365,204 | 12/1982 | Hague | 328/127 |
| 4,446,715 | 5/1984 | Bailey | 73/1 R |
| 4,481,596 | 11/1984 | Townzen | 364/571 |
| 4,482,261 | 11/1984 | Dewey et al. | 374/134 X |
| 4,588,308 | 5/1986 | Saito | 374/181 |
| 4,669,049 | 5/1987 | Kosedenar et al. | 374/182 X |
| 4,785,250 | 11/1988 | Lawton | 328/128 X |

FOREIGN PATENT DOCUMENTS 1085366  2/1955  France .................. 374/181

OTHER PUBLICATIONS

Article Entitled, "Any Voltmeter Reads Electronic Thermometer" by Robert J. Battes, Designer's Casebook; Electronics, Sep. 5, 1974.
Hewlett Packard Article-1969 Electronics for Measurement-Analysis-Computation, pp. 57, 62, 149, 151.
Article Entitled, "Voltage-Controlled Resistance Switches Over Preset Limits," by Chris Tocci, Electronics/Sep. 25, 1980, p. 133.
Article Entitled, "Instantaneous-Frequency Meter Measures Biomedical Variables," by Barnett/Millar; Electronics, Aug. 30, 1979, p. 143.
Article Entitled, "RC Oscillator Linearizes Thermistor Output," by B. Sundquist, Electronics, Jan. 13, 1983, p. 169.
Article Entitled, "Dual-Function Amp Chip Simplifies Many Circuits," by Jim Williams, Electronics, May 5, 1981, pp. 142, 143-146.
Mon-A-Therm Temperature Monitoring System--Product Catalog of Mon-A-Therm, Inc. St. Louis, Missouri, Showing Disposable Sensors.
"Switched Capacitors Unlock Filters," Electronic Design News, Apr. 3, 1986, pp. 142-143.
"Monolithic CMOS-Switch Suits Diverse Applications," by Jim Williams, Electronic Design News, Oct. 4, 1984, pp. 183-194.

Primary Examiner—Daniel M. Yasich
Attorney, Agent, or Firm—Price, Gess & Ubell

[57] ABSTRACT

Temperature measurement with thermocouples is made more accurate, and the cost of disposable thermocouples is reduced by locating the cold junction close to the hot junction, utilizing a thermistor in thermal communication with the cold junction in developing a compensating voltage which varies with temperature as does the voltage produced by the cold junction, and applying the compensating voltage to cancel the cold junction voltage. The presence of radio frequency fields in the region of the thermocouple is detected and utilization of the thermocouple voltage is interrupted in intervals when the interference is greater than some preselected intensity. Further, the thermocouple voltage information is utilized to simulate the resistance a thermistor would have at the temperature represented by the thermistor voltage information and that simulated resistance is applied to instrumentation designed to measure temperature with a thermistor.

8 Claims, 2 Drawing Sheets

TEMPERATURE MEASUREMENT

This invention relates to improvements in temperature measurement, and in particular to improved compensation, diminution of radio frequency interference and improved signal processing in temperature measuring systems which employ thermocouples.

BACKGROUND

While the invention has other applicability it is especially suited to the measurement of temperature in medical and veterinary applications. Measurement is accomplished with a probe which is connected to a signal processing and indicating unit to form the measurement system. For practical reasons it is the practice that the probe be made disposable and not reused. The measurement is made electrically. The probe provides an electrically measurable signal which varies as a function of temperature. Two forms of sensor are in common use: one is a thermistor, the resistance of which varies with temperature; the other is a thermocouple in which potentials are developed which are a function of temperature.

Thermocouple probes are less costly than are thermistor probes. Because the probes are not reused the lower cost thermocouple variety is preferred, except that it presents technical problems which tend to increase cost. Unlike the thermistor probe which provides a direct indication of temperature, the thermocouple probe senses the difference in temperature at the hot and cold junctions of the thermocouple whereby some form of compensation is required to convert the measurement of temperature difference to temperature. Past solutions to that problem have added to the cost of the thermocouple probe.

Further, existing instrumentation designed for use with thermistor probes is not compatible with the thermocouple probe. Accordingly, there has been a need, not only for improvement in thermocouple probe systems, but the need extends to finding a solution that would permit use of the improved thermocouple probe with the thermistor probe instrumentation.

Another difficulty arises out of the fact that the temperature-sensing probe may be located at a substantial distance from the signal processing and indicating apparatus with which it is associated. In the hospital and clinical environments in particular, where x-ray machines and other radio frequency generating apparatus creates very strong fields, radio frequency interference with temperature measurement is a difficult and serious problem. The traditional bypassing and radio frequency choking techniques are less than adequate, and the problem is amplified by the compensating techniques heretofore employed in connection with thermocouple sensing.

SUMMARY OF THE INVENTION

One object of the invention is to provide improved methods and means for measuring temperature with the aid of a thermocouple.

Another object is to provide improvements in the compensation of thermocouple sensors.

Another object is to provide improvements in overcoming the effect of radio frequency interference in temperature-measuring systems.

A further object is to provide an improved means for making possible the utilization of a thermocouple probe with instrumentation designed for use with a thermistor probe.

These, and other objects and advantages of the invention which will become apparent upon inspection of the specification which follows and the accompanying drawings, are realized in part by the provision of a thermocouple circuit comprising a hot junction and a cold junction connected in series circuit together with signal processing means for producing a simulated resistance whose value is indicative of the temperature at the thermocouple circuit; the signal processing means comprising resistance simulating means in the form of a capacitor and a variable rate pulse generator connected to charge the capacitor to a potential which is a function of said temperature.

Further the invention can be described as including a thermocouple comprising a hot junction and a cold junction connected in series in a thermocouple circuit together with a compensating means comprising a thermistor disposed in thermal proximity to the cold junction for generating a compensating potential corresponding, within a predetermined range of temperatures, to a potential developed at the cold junction, and also including means for including the compensating potential in the thermocouple circuit in opposition to the potential developed at the cold junction.

Further, the invention envisions the combination of the cold junction and a compensating thermistor being disposed in physical proximity to the hot junction whereby the length of the disposable portion of the thermocouple is short and consequently less costly than prior disposable units.

Also, the invention extends to a temperature measuring system which incorporates a thermocouple comprising a hot junction and a cold junction connected in series in a thermocouple circuit, or a thermistor sensor, together with signal processing means connected to the thermocouple for providing periodic indications of the temperature currently being sensed by said thermocouple. A radio frequency detection means for detecting, and for providing disabling signals, in intervals during which said radio frequency field intensity is greater than some predetermined magnitude in the vicinity of the said thermocouple is employed along with a disabling means responsive to the disabling signals for rendering the signal processing means effective to provide indications of current temperature during such intervals.

THE DRAWINGS

FIG. 1. is a schematic drawing which illustrates a basic thermocouple system of the kind employed in the invention;

FIG. 2. is a partly schematic and partly diagrammatic showing of a preferred form of the invention; and FIG. 3. is a cross-sectioned schematic view of a thermocouple employed in the invention.

DESCRIPTION OF THE PREFERRED EMBODIMENT

Figure 1:
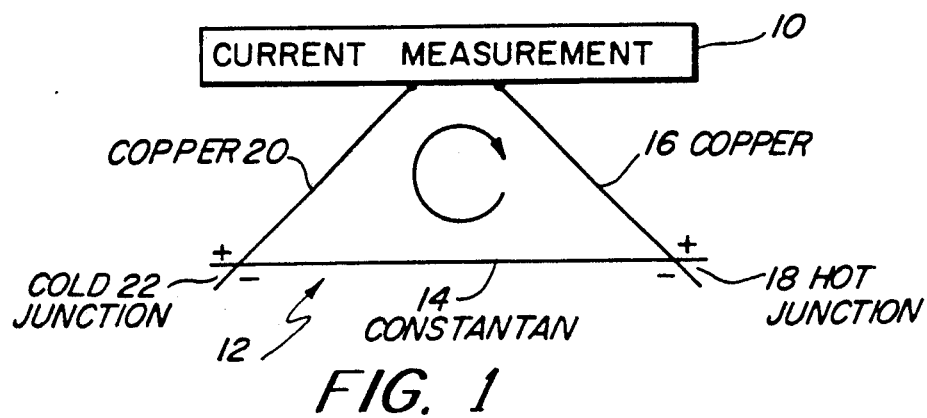

The German physicist, Thomas J. Seebeck, discovered thermoelectricity at the turn of the nineteenth century. The thermoelectric or Seebeck effect is attributed largely to the contact potentials at the junction of dissimilar metals. When a circuit is formed of two wires of different metals and one of their junctions is at higher temperature than the other, an electromotive force is produced in the circuit. Ideally, one of those junctions is maintained at a known temperature, and the other junction is subjected to a temperature whose value is to be determined. The first of those junctions is conventionally called, the "cold junction," and the other is called, the "hot junction." The potential developed in the circuit is the measure of the difference between the temperatures at the hot and cold junctions. Thus, the temperature at the hot junction is found by adding the differential temperature to the known temperature at the cold junction.

In practice it is often impractical to maintain the cold junction at a fixed, known temperature. In that circumstance it is necessary to measure the temperature at the cold junction or to provide some appropriate compensation.

The magnitude of the potentials that are developed in a thermocouple circuit and the degree of linearity with which those potentials change with temperature varies with the materials used in forming the junction. The combination of copper and constantan results in linear change in voltage with temperature over the range of temperatures that are of interest in the medical and veterinary fields and are almost universally used in thermocouples intended for those fields. They are the preferred materials for use in practicing the invention. The hot junction is formed by interconnecting a copper wire with a constantan wire. To complete the electric circuit the wires must be joined together at a second junction or the circuit completed by connection through additional conductors. That second junction, or the combination of the additional junctions, forms the cold junction. To avoid the complication that would result from additional junctions of dissimilar materials, it is the practice to locate the second junction and any additional junctions at a common point in the signal-processing unit to which the thermocouple is connected. That practice leads to a construction in which the constantan wire extends the entire distance from the hot junction where temperature is to be measured to the signal-processing unit. In practice that is a significant distance; it may be six feet, or more, between the point of temperature measurement and the signal-processing unit. That gives rise to two difficulties. One is that thermocouple wires act as a receiving antenna by which radio frequency interference is introduced into the measurement system. Those interfering signals may have magnitudes which approach that of the temperature induced voltages. The other problem is that the cost of an elongated constantan and copper wire cable is substantial, in view of the fact that they are not reused.

The invention provides a way to solve both of those problems. The cold junction is moved into relatively close proximity with the hot junction. A thermistor disposed in thermal proximity to the cold junction is employed to develop a voltage which varies with temperature as does the voltage at the cold junction, or substantially so. The cold and hot junctions are in series circuit. The potentials developed at those junctions are opposed in polarity. The compensating potential developed with the aid of the thermistor is included in that series circuit such that it opposes the potential produced at the cold junction. The compensating potential is equal to, and opposite in polarity to the cold junction potential. Consequently, the potential in the thermocouple circuit which is presented to the cable that extends from the junctions to the signal-processing unit is only the potential produced at the hot junction. The sensor has been converted to one which, like the thermistor sensor, measures temperature directly. The preferred means by which that result is accomplished is depicted at the left in FIG. 2 and in FIG. 3.

The basic circuitry of a copper-constantan thermocouple system is shown in FIG. 1. It includes a current measurement device 10 and a thermocouple, generally designated 12. The latter includes a constantan wire 14, one end of which is connected to one end of a copper wire 16 to form a hot junction 18. The other end of the constantan wire 14 is connected to one end of a second copper wire 20 to form a cold junction 22. The other ends of the two copper wires 16, 20 are connected to the current measurement instrument 10 where the thermocouple circuit is completed. It is assumed in FIG. 1 that the hot junction 18 and the cold junction 22 are at temperatures in the normal operating range of the system, in which case the copper side of the hot junction 18 is positive with respect to the constantan side 14. At the cold junction 22 the potential is less; the constantan side 14 is negative with respect to the copper side 20. Current flow in the thermocouple circuit will be clockwise for the conditions described.

Figure 2:
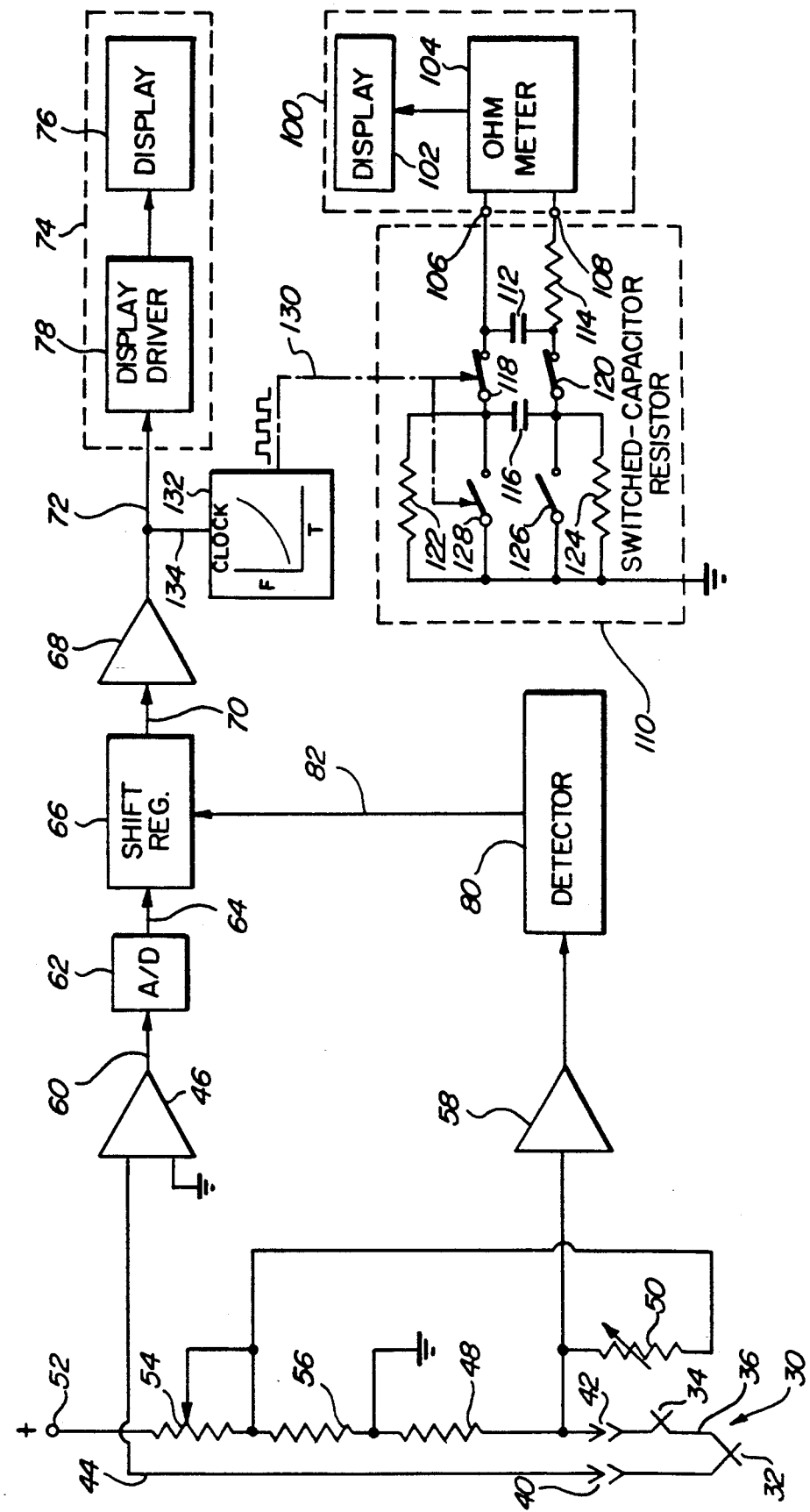

In FIG. 2, the thermocouple is generally indicated by the numeral 30. The hot junction 32 and the cold junction 34 are in relatively close proximity. Leg 36 is made of constantan. Leg 38 is copper. The other side of the cold junction 34 attached to a connector 42 is copper. The circuit is arranged for disconnection on both sides by a connector 40 at the left and the connector 42 at the right. The short portion of the circuit below connectors 40 and 42 is the disposable temperature measuring probe. From connector 40, the thermocouple circuit continues by copper line 44 to the input of an analog amplifier 46. At the other side of the circuit, the continuity is completed above connector 42 through resistor 48 to ground and from ground to the other input terminal of the amplifier 46.

The numeral 50 identifies a thermistor which is disposed in thermal proximity to the cold junction 34 so that the temperature to which the cold junction and the thermistor 50 are subjected is substantially the same. That thermistor 50 is connected in a circuit which extends from a positive reference voltage source 52 through a variable resistor 54 to ground through the parallel combination of a resistor 56 and the series circuit combination of the thermistor 50 and the resistor 48. The junction between the thermistor 50 and the resistor 48 is connected to the connector 42, at the side away from the cold junction 34, and is connected to the input of a radio frequency amplifier 58. Amplifier 58 has a bandwidth sufficient to pass and amplify radio frequency signals whose frequency corresponds to the frequency of radiations that emanate from laser power supplies, x-ray machines, cauterizing apparatus, and the like, which are commonly found in the medical and the veterinary fields. Amplifier 58 may comprise a conventional TLC 2512 CP operational amplifier, as manufactured by Texas Instruments.

The output of the analog amplifier 46 is applied by line 60 to an analog-to-digital converter 62. The output of that converter is applied by line 64 to a shift register 66. The converter 62 and shift register 66 may comprise a conventional TLC 14511N circuit, as manufactured by Texas Instruments. The output of the shift register 66 is applied to a digital amplifier 68 by line 70. The output of the digital amplifier 68 is applied by line 72 to the input of a display unit 74 which comprises a display 76 and a display driver 78 of a kind that is suitable to drive the selected display, such as the MM5452 display driver, as manufactured by National Semiconductor.

The output of the radio frequency amplifier 58 is applied to a radio frequency detector 80 which rectifies, and applies detected signals having greater than a predetermined amplitude to output line 82. The detector 80 may be a IN4149 silicon diode.

The output line 82 is connected to the shift register 66. Signals on that line 82 serve to disable the shift register 66 so that, during an interval when radio frequency interference signals have sufficient amplitude to produce an output on line 82, the shift register 66 is inoperative to transfer temperature signals from the analog-to-digital converter to amplifier 68. The input of the radio frequency amplifier 58 is not necessarily connected to the temperature sensing circuitry. A wire in the sensing circuit cable, or any other arrangement which serves as an antenna, may be used to provide an indication of the radio frequency field intensity in the region of the temperature sensing circuitry. In some cases, that arrangement is preferred because the measured intensity will be independent of the value of the thermistor and of temperature.

The circuits thus far described comprise the combination of a thermocouple and thermocouple-type signal processing and display unit. They incorporate temperature compensation and radio frequency interference deletion according to the invention. In addition, the output of the scale-changing amplifier 68 can be made to drive a signal processing and display unit of a kind which is suitable for use with thermistor sensors. Such a signal processing and display unit is included in the circuit of FIG. 2, where it is numbered 100 and comprises a display, unit 102 driven by an ohm meter 104. The input terminals of the ohm meter are numbered 106 and 108.

A special circuit generally designated 110 is connected across terminals 106 and 108. It includes a capacitor 112 and a resistor 114 which are connected in series, in that order, from terminal 106 to terminal 108. A second capacitor 116 is connected in parallel with capacitor 112 through a pair of switches 118 and 120. Switch 118 connects the upper side of the two capacitors in the diagram, and switch 120 connects their lower sides. Each side of capacitor 116 is connected to ground through a respectively associated calibrating resistor. The resistor that is in series with switch 118 is numbered 122. The resistor that is in series with switch 120 is numbered 124. A switch 126 is connected to short circuit resistor 124 when closed. A switch 128 is connected to short circuit resistor 122 when closed. Switches 118 and 120 open and close together, as do switches 126 and 128. When switches 118 and 120 are closed, switches 126 and 128 are open and vice-versa. In the preferred embodiment switches 118, 120, 126 and 128 may be Part No. LTC1043CN, as manufactured by Linear Technologies Corp. of Milpitas, Calif., and form part of a solid state switching arrangement of which capacitor 116 is another part. The solid state switching arrangement is usually referred to as "switched-capacitor resistors." Such a circuit mimics the behavior of a resistor. Together with capacitor 112 and resistor 114, the switched-capacitor resistor emulates a resistor whose effective value is determined by the rate at which the several switches of the switched-capacitor resistor are actuated. The switches are solid state, CMOS devices. To facilitate understanding, they have been shown with symbols that indicate equivalent mechanical switches.

The dashed line 130 indicates that the switches 126, 128 are actuated by pulsed signals generated in a clock 132. The pulse repetition rate or frequency applied by the clock 132 to the switches is selected by the magnitude of the signal on line 134, which is connected to the output of amplifier 68. Accordingly, the clock 132 may comprise a variable rate pulse generator such as the P82C54 programmable timer manufactured by Intel or Fujitsu. The signal on line 134 varies as a linear function of temperature. The frequency or pulse repetition rate of the clock output is a nonlinear function of the signal on line 134. It varies approximately as shown in the graph within clock block 132 to match the characteristics of circuit 110 and, more particularly, the published characteristics of the switched-capacitor resistor. As an alternative to pulse repetition rate, pulse width modulation or some other equivalent may be employed. Circuit 110 and pulse generator 132 may be viewed as a means for generating a resistance of varying value, the overall result being a resistance which, as mentioned above, emulates or simulates the output one would see from a thermistor.

While the clock 132, scale-changing amplifier 68, and shift register 66 are shown as discrete units, it is possible to perform equivalent functions, or any one of them, in a microprocessor and, in some applications, that would be preferred. It will be appreciated from the foregoing that amplifier 46, shift register 66, amplifier 68, clock 132, and switched-capacitor resistor circuit 110 comprise signal processing means for providing a resistance value indicative of the temperature at the thermocouple, and which simulates a thermistor output. Clock 132 may be viewed as generating a switching signal comprising the pulse train on line 130, which causes circuit 110 to develop a resistance which simulates a thermistor output.

Figure 3:
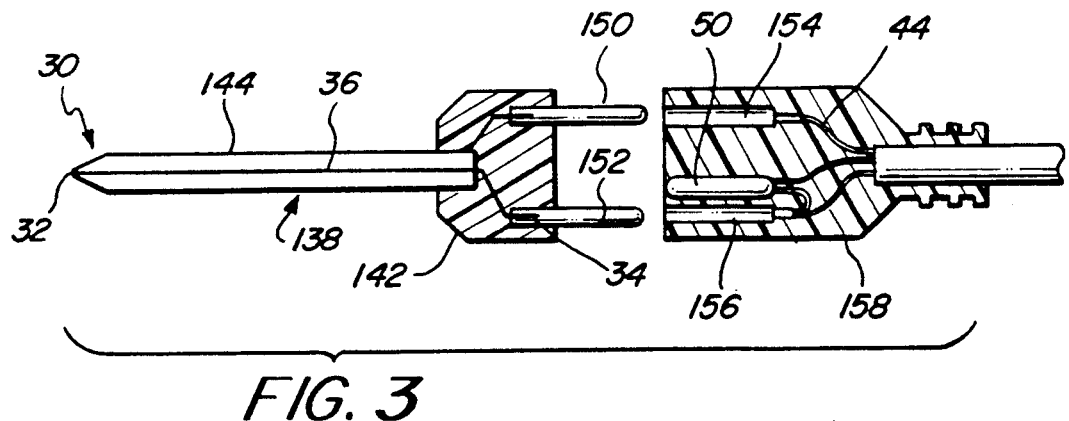

FIG. 3 illustrates the structural arrangement by which the disposable probe 138 is connected to the remainder of the system and how the thermistor 50 is associated with the cold junction 34. The constantan leg 36 of the thermocouple terminates at the left of FIG. 3 in a connection to a protective, conductive sheath 144 which, in FIG. 2, is leg 38. The juncture at the far left of FIG. 3 is the hot junction. The sheath 144 is fixed in a two-pronged plug 142 and is connected electrically to prong 150. Both the sheath 144 and the prong 150 are made of copper. Leg 36 is made of constantan. It extends through the sheath 144 to a connection to copper prong 152 of the plug 142 and formation of the cold junction 34. Prongs 150 and 152 mate with sockets 154 and 156, respectively, which are embedded in socket member 158. The thermistor 50 is disposed in a cavity formed in the socket member 158, where it is in thermal contact with the cold junction 34. It will be apparent that the disposable probe 138 is both simple and inexpensive.

We claim:

1. For connection to a temperature measuring instrument designed to receive as an input the resistance developed by a thermistor probe, said resistance varying in a nonlinear manner with the temperature at said probe, in combination:

a thermocouple circuit means for developing a potential related to the ambient temperature at said circuit means, said circuit means comprising a hot junction and a cold junction connected in a series circuit; and signal processing means responsive to said potential for producing a resistance value which simulates the resistance developed by said thermistor probe at said ambient temperature;

said signal processing means including means for generating said resistance value, said resistance generating means comprising a capacitor and a variable rate pulse generator connected to charge the capacitor to a potential which is a function of said ambient temperature;

whereby said temperature measuring instrument is adapted to operate with said thermocouple circuit means.

2. The method of processing thermocouple voltage information for application to apparatus capable of interpreting the resistance information provided by a thermistor probe, said thermocouple voltage information being indicative of a selected temperature under measurement, which method comprises the steps of:
a) converting said thermocouple voltage information to digital information;
b) generating a switching signal in response to said digital information; and
c) utilizing said switching signal to switch a switched-capacitor resistance to develop a resistance value which simulates said resistance information.

3. For connection to a temperature measuring instrument designed to receive as an input the resistance developed by a thermistor probe having a known nonlinear resistance versus temperature characteristic, in combination:
a thermocouple circuit means for developing a potential related to the ambient temperature at said circuit means, said circuit means comprising a hot junction and a cold junction connected in a series circuit; and
signal processing means responsive to said potential for producing a resistance value which simulates the resistance of said thermistor probe at said ambient temperature, said signal processing means including:
a switched-capacitor resistor circuit means responsive to a periodic switching signal of selected frequency for generating said resistance value; and
a variable rate pulse generator means for generating said switching signal and selecting the frequency of said switching signal to generate said resistance value in accordance with said known nonlinear characteristic of said thermistor probe;
whereby said temperature measuring instrument is adapted to operate with said thermocouple circuit means.

4. The combination of claim 3 wherein said means responsive to a switching signal comprises:
a capacitor; and
means responsive to said switching signal for connecting said capacitor to ground, whereby said capacitor operates as a shunt resistive element.

5. The combination of claim 3 further including means responsive to radio frequency signals for disabling operation of said signal processing means.

6. The combination of claim 5 wherein said means responsive to radio frequency signals includes:
radio frequency amplifier means having an input for amplifying a radio frequency signal supplied to said input;
means for supplying a radio frequency signal to said input; and
means for detecting a signal at the output of said amplifier means greater than a selected amplitude and disabling said signal processing means upon said detection.

7. The combination of claim 6 wherein said signal processing means includes a shift register and said means responsive to radio frequency signals disables said shift register in response to detection of a said signal greater than a selected amplitude by said means for detecting.

8. The combination of claim 5 wherein said signal processing means includes a shift register and said means responsive to radio frequency signals disables said shift register in order to disable said signal processing means.

* * * * *

UNITED STATES PATENT AND TRADEMARK OFFICE
CERTIFICATE OF CORRECTION

PATENT NO. : 5,066,140

DATED : November 19, 1991

INVENTOR(S) : Gordon Y. Shigezawa, et al

It is certified that error appears in the above-identified patent and that said Letters Patent is hereby corrected as shown below:

On the Title Page:

Item [19] should read --Shigezawa, et al--.

Item [75], Inventors should read --Gordon Y. Shigezawa, Irvine, Calif.; Anthony V. Beran, Santa Ana, Calif.

Signed and Sealed this

Sixteenth Day of March, 1993

*Attest:*

STEPHEN G. KUNIN

*Attesting Officer*     *Acting Commissioner of Patents and Trademarks*